United States Patent [19]

Su et al.

[11] Patent Number: 5,858,999
[45] Date of Patent: Jan. 12, 1999

[54] COSOLVENT PARENTERAL FORMULATION OF TIRILAZAD

[75] Inventors: Ching-Chiang Su, Portage, Mich.; David S. Baker, Schoolcraft, Mich.; Susan M. Machkovech, Mattawan, Mich.

[73] Assignee: Pharmacia & Upjohn Company, Kalamazoo, Mich.

[21] Appl. No.: 875,217

[22] PCT Filed: Aug. 29, 1995

[86] PCT No.: PCT/US95/10730

§ 371 Date: Jan. 4, 1997

§ 102(e) Date: Jan. 4, 1997

[87] PCT Pub. No.: WO96/06618

PCT Pub. Date: Mar. 7, 1996

Related U.S. Application Data

[63] Continuation of Ser. No. 382,256, Feb. 1, 1995, abandoned, which is a continuation-in-part of Ser. No. 299,370, Sep. 1, 1994, abandoned.

[51] Int. Cl.[6] .......................... A61K 31/58; A61K 31/50; A61K 31/495; A61K 31/40
[52] U.S. Cl. .......................... 514/176; 514/247; 514/249; 514/408
[58] Field of Search .................................... 514/169, 176, 514/247, 249, 408

[56] References Cited

U.S. PATENT DOCUMENTS

| | | | |
|---|---|---|---|
| 4,794,117 | 12/1988 | Corbiere | 514/420 |
| 4,968,675 | 11/1990 | Su | 514/176 |
| 5,124,154 | 6/1992 | Babcock et al. | 424/427 |
| 5,175,281 | 12/1992 | McCall et al. | 540/94 |
| 5,614,515 | 3/1997 | Rodgers et al. | 514/176 |

FOREIGN PATENT DOCUMENTS

| | | | |
|---|---|---|---|
| 85/04106 | 9/1985 | WIPO | A61K 47/00 |
| 87/01706 | 3/1987 | WIPO | C07J 41/00 |

OTHER PUBLICATIONS

The Journal of Pharmacology & Experimental Therapeutics, 269, 145–50 (1994).
International Journal of Clinical Pharmacology & Therapeutics, 32, 223–230 (1994).
Pharmaceutical Research, 11(2) 341 (1994).
Solubilization of Drugs by Cosolvents, "Techniques of Solubilization of Drugs", edited by S. H. Yalkowsky, Marcel Dekker, INC., pp. 91–134 (1981).
Journal of Pharmaceutical Science and Technology, 48, pp. 86–91 (1994).

*Primary Examiner*—Kevin E. Weddington
*Attorney, Agent, or Firm*—Bruce Stein

[57] ABSTRACT

The invention is a cosolvent parenteral pharmaceutical formulation of a lazaroid and its pharmaceutically acceptable salts.

17 Claims, No Drawings

COSOLVENT PARENTERAL FORMULATION OF TIRILAZAD

This application is a 371 of PCT/US95/107308 filed Aug. 29, 1995 and a continuation of Ser. No. 08/382,256 filed Feb. 1, 1995; now abandoned which is a CIP of Ser. No. 08/299,370 filed Sep. 1, 1994; now abandoned.

BACKGROUND OF THE INVENTION

1. Field of the Invention

The invention is a cosolvent parenteral pharmaceutical formulation of lazaroid compounds.

2. Description of the Related Art

International Publication No. WO87/01706 based on International Patent Application No. PCT/US86/01797 and U.S. Pat. No. 5,175,281 disclose 21-[4-[2,6-bis(1-pyrrolidinyl)-4-pyrimidinyl]-1-piperazinyl]-16α-methylpregna-1,4,9(11)-triene-3,20-dione (EXAMPLE 83), which is known as tirilazad, and the mesylate salt (EXAMPLE 109) which is known as tirilazad mesylate for use as neurological agents.

The Journal of Pharmacology and Experimental Therapeutics, 269, 145–50 (1994), International Journal of Clinical Pharmacology and Therapeutics, 32, 223–230 (1994) and Pharmaceutical Research, 11(2) 341 (1994) disclose 21-[4-[2,6-bis(1-pyrrolidinyl)-4-pyrimidinyl]-1-piperazinyl]-16α-methyl-5α-pregna-1,9(11)-diene-3,20-dione (5α-tirilazad).

U.S. patent application Ser. No. 08/278,633 discloses 21-[4-[2,6-bis(1-pyrrolidinyl)-4-pyrimidinyl]-1-piperazinyl]-16α-methyl-5α-pregna-1,9(11)-diene-3,20-dione (5α-tirilazad) and the 5β-isomer (5β-tirilazad) and pharmaceutically acceptable salts thereof.

U.S. patent application Ser. No. 08/361,818 discloses 6α-hydroxy-21-[4-[2,6-bis(1-pyrrolidinyl)-4-pyrimidinyl]-1-piperazinyl]-16α-methylpregna-1,4,9(11)-triene-3,20-dione (6α-hydroxytirilazad) and 6β-hydroxy-21-[4-[2,6-bis(1-pyrrolidinyl)-4-pyrimidinyl]-1-piperazinyl]-16α-methylpregna-1,4,9(11)-triene-3,20-dione (6β-hydroxytirilazad) and pharmaceutically acceptable salts thereof.

U.S. Pat. No. 4,968,675 discloses a parenteral formulation of tirilazad mesylate in citrate buffer. The present invention in addition uses a cosolvent which causes less irritation and pain when used as intended (diluted).

Cosolvents have become widely used as a means for solubilizing drugs for non-parenteral and parenteral (both IV and IM) administration. The effect is dependent primarily upon the polarity of the drug with respect to the solvent (water) and the cosolvent. The degree to which the solubility of a drug can be increased for a particular cosolvent is dependent upon the nonpolarity of the drug and the nonpolarity of the cosolvent. The most frequently used cosolvents are propylene glycol, ethanol, glycerine, and polyethylene glycol. The solubilization curves of a number of pharmaceutically important solutes in cosolvent systems is known, Techniques of Solubilization of Drugs, edited by S. H. Yalkowsky, Marcel Dekker, INC 1981, more particularly see Solubilization of Drugs by Cosolvents, p 91–134.

U.S. Pat. No. 4,794,117 and International Publication No. WO85/04106 disclose that solubilization of hydrophobic pharmaceuticals, e.g. steroids, may be accomplished by solution in polyethylene glycol and addition of aqueous solutions of controlled pH and buffering.

Buffers in parenteral formulations are known.

Journal of Pharmaceutical Science and Technology, 48, 86–91 (1994) discloses that for that particular drug lower acetate buffer concentration caused less irritation than higher acetate buffer concentration. It was further disclosed that citrate buffer concentration of 0.01M caused less irritation than acetate buffer concentration at 0.005M with the particular drug used.

SUMMARY OF INVENTION

Dislosed is a sterile aqueous pharmaceutical composition for parenteral administration which comprises:

(1) about 0.9 to about 90 mg/ml of a lazaroid or a pharmaceutically acceptable salt thereof, (2) about 0.002 to about 2.0M citrate, (3) up to about 80% of a cosolvent selected from the group consisting of propylene glycol, polyethylene glycol, glycerol, ethanol, DMSO, DMAC, DMI and M-PYROL, (4) water at a pH of about 2.4 to about 3.5.

Also disclosed is a sterile aqueous pharmaceutical composition for parenteral administration which comprises:

(1) 25 mg/ml of 21-[4-[2,6-bis(1-pyrrolidinyl)-4-pyrimidinyl]-1-piperazinyl]-16α-methylpregna-1,4,9(11)-triene-3,20-dione mesylate, (2) 0.25M citrate, (3) 40% propylene glycol, (4) water at a pH of about 2.7 to about 3.1.

DETAILED DESCRIPTION OF THE INVENTION

The pharmaceutical agents tirilazad, 5α-tirilazad, 5β-tirilazad, 6α-hydroxytirilazad, 6β-hydroxytirilazad and pharmaceutically acceptable salts will be collectively referred to as "lazaroids". It is preferred that the lazaroid be tirilazad; it is more preferred that the lazaroid be tirilazad mesylate.

Lazaroids are useful in treating and/or preventing spinal injury mild and/or moderate to severe head injury, subarachnoid hemorrhage (SAH) and subsequent ischemic stroke, asthma and reduction of mucous formation/secretion in the lung, muscular dystrophy, adriamycin cardiac toxicity, Parkinsonism, other degenerative neurological disorders, multiple sclerosis, organ damage during reperfusion after transplant, preservation of transplant organs by treatment of the donor, skin graft rejection, hemorrhagic, traumatic and septic shock, and conditions such as severe burns, ARDS, chemical oxidant-induced injury to the kidney (for example, inhibition of contrast dye nephropathy and inhibition of cyclosporine toxicity) nephrotic syndrome (immunological), systemic lupus erythematosus, allergic reactions, atherosclerosis, inflammation (dermatological antiinflammatory and antipsoriasis agents), emphysema, cancer (limit metastasis, limit tumor growth), (stress induced) ulcers, ulcerative colitis and Crohn's disease. The lazaroids are also useful for prophylactic treatment before surgical procedures such as hip and jaw surgery where the lazaroids reduces edema. They are useful for preventing neurologic injury during surgical procedures and neurological procedures, for treatment of myocardial infarctions, for treatment after resuscitation to improve outcome, particularly neurological outcome post resuscitation, drug allergic reactions and migraine headaches. The compounds have use in ophthalmology, e.g., in treatment of diabetic retinopathy, age-related macular degeneration, cataracts and glaucoma, light-induced retinal damage and in irrigation mixtures used in eye surgery, prevention of hyperoxic injury in adults and infants, reduction of facial edema after surgical procedures such as oral/facial surgery or trauma from accidents. The lazaroids also can be co-administered with anti-cancer drugs such as adriamycin, taxol or vinblastine when the tumor or cell strain becomes resistant as the lazaroids are effective inhibitors of multiple drug resistance. The lazaroids are also useful in protection from radiation injury, particularly in brain and gut. In case of the gut, the lazaroids can be administered topically (e.g. by suppository) or by other more common routes. This is particularly helpful in preventing gut injury during prostate irradiation.

In humans, the lazaroids are useful in treating subarachnoid hemorrhage and subsequent cerebral vasospasm, global cerebral ischemia post resuscitation (CPR) to prevent post-ischemic brain damage, brain tumor (neuroprotective), Bells Palsy, other degenerative neurological disorders, hepatic necrosis (e.g. from viral hepatitis), some forms of radiation damage (for example during radiation treatment or from accidental exposure to radiation), myocardial damage after myocardial ischemia, pre-birth infant strangulation and infant hypoxia syndrome, such ophthalmic disorders as uveitis and optic neuritis and ischemic bowel syndrome.

In humans, the lazaroids are useful in preventing damage following—cardiopulmonary resuscitation, neurological or cardiovascular surgery and from cardiac infarction, ocular damage after ophthalmic surgery (e.g. cataritic surgery).

It is preferred that the lazaroids are useful in treating complications of surgery or trauma such as edema and neurologic injury and renal injury. Generally, the lazaroids are used like the glucocorticoid pharmaceuticals for the treatment of the above human conditions as well as the animal conditions listed below. While lazaroids are useful in both humans and animals in treating many of the same conditions and preventing complications and damage from the same problems as the glucocorticoids, lazaroids are useful in treating a number of conditions and preventing damage from conditions where the glucocorticoids are not useful. Lazaroids have no glucocorticoid activity and therefore, unlike the glucocorticoids, they can be given daily for longer periods of time without the side effects associated with the glucocorticoids. This is a distinct advantage. They have no effect on blood glucose and this is also an advantage.

It is to be understood that lazaroids will be more useful to a different degree to treat some of these conditions than others.

The standard conditions for treatment are to give lazaroids orally or parenterally, e.g. IV (that is by injection, infusion or continuous drip) or IM, with a standard dose of about 5 to about 20 mg/kg/day IV for up to 20 days (with 10 days being sufficient for some conditions) or about 5 to about 30 mg/kg/day; one to four times daily by mouth. Females may be given higher doses than males since, on the average, they may metabolize lazaroids more rapidly than males. For females the standard dose is from about 7 to about 30 mg/kg/day IV or about 7 to about 50 mg/kg/day one to four times daily by mouth. For example, in treatment of SAH males may be give 10 mg/kg/day and women given 15 mg/kg/day. The dose can be administered as a single injection or, more typically, by divided doses (usually three or four times daily).

In treating SAH the patient should be treated with from about 6 mg/kg/day to about 20 mg/kg/day, preferably from about 10 to about 15 mg/kg/day.

In treating mild and moderate to severe head injury the patient should be treated with from about 10 mg/kg/day to about 20 mg/kg/day, preferably from about 10 to about 15 mg/kg/day.

In treating ischemic (thromboembolic) stroke the patient should be treated with an initial dose of from about 10 to about 25 mg/kg on day one, preferably from about 12.5 mg (males) and 15 mg (females) to about 20 mg/kg, to be followed by about 10 mg (males) and about 12.5 mg/kg (females) to about 20 mg/kg for about 3 days.

In treating spinal cord injury the patient is treated with about 5 to about 20 mg/kg/day for one to a few days. It is preferable to treat those with spinal cord injury with about 10 to about 20 mg/kg/day for one day. When treating patients with spinal cord injury it is also preferable to give them a one time large dose of a steroid such as methylprednisolone sodium succinate prior to the administration of the lazaroids.

For treating damage following cardiopulmonary resuscitation, cardiac infarction, organ damage during reperfusion after transplant, hemorrhagic, traumatic and septic shock, severe burns, ARDS, and nephrotic syndrome and preventing skin graft rejection, the standard conditions are used. Typical treatment may involve an initial loading dose, e.g. an IV dose of 0.05 mg to 4 mg/kg followed by maintenance dosing usually given four times a day by IV bolus infusion for one to 10 days depending on the particular condition of the patient and the particular compound used. This may be supplemented with IM or oral dosing for days, weeks or months.

In treating inflammatory lung maladies such as asthma, lazaroids are administered orally, IV and by inhalation in the standard dose. In treating excess mucous secretions, the oral dose of lazaroids are from about 5 to about 30 mg/kg/-day. The frequency of administration is one through 4 times daily. The oral administration of lazaroids to treat excess mucous secretions may go on for months or even years. The susceptible individuals can be pre-treated a few hours before an expected problem. The IV dose is about 5 to about 20 mg/kg/day. The aerosol formulation contains about 0.01 to about 1.0% of lazaroids are administered or used about four times daily as needed. In treating muscular dystrophy, Parkinsonism, and other degenerative neurological disorders (amyotrophic lateral sclerosis; multiple sclerosis) lazaroids are administered orally using a dose of about 5 to about 30 mg/kg/day, administered or used one to four times a day. The treatment may go on for years.

In treating adriamycin-induced cardiac toxicity, lazaroids are administered orally or IV using a dose of about 1.0 to about 50 mg/kg/day, preferably about 5 to about 20 mg/kg/day. Lazaroids are preferably given concomitantly with IV adriamycin or the individual is pre-treated with lazaroids.

For prophylaxis prior to and preventing damage after neurological or cardiovascular surgery, lazaroids are used according to the standard conditions. The patient can be pretreated with a single IV or IM dose just prior to and after surgery or orally before and after surgery.

In treating drug allergic reactions, lazaroids are given in a dose of about 5 to 20 mg/kg/day, administered one to four times daily IV and about 5 to about 30 mg/kg/day orally. Typical treatment would be an initial IV loading dose followed by oral dosing for a few days or more.

In treating atherosclerosis and emphysema, lazaroids are given orally in a dose of about 5 to about 30 mg/kg/day, one to four times daily for months or years. Lazaroids are useful in treatment of premature infants who may be maintained in a high oxygen environment. Lazaroids improve morbidity and mortality in these cases which are particularly susceptible to intracranial bleeding and bronchopulmonary dysplasia. In this situation the standard treatment is given either IV or orally.

In treating dermatological inflammatory conditions including psoriasis, lazaroids are given orally in a dose of about 5 to about 30 mg/kg/day, once or the amount can be given two to four times daily in divided doses or applied topically as a cream, ointment or lotion or equivalent dosage form in a concentration of about 0.05 to about 5% as long as needed. In treating these conditions lazaroids can be used with steroidal agents.

Lazaroids are useful in the prevention and treatment of stress ulcers and of gastric intolerance caused by drugs such as nonsteroidal anti-inflammatory compounds (NOSAC). Stress ulcers are ulcers that develop after exposure to severe conditions such as trauma, burns, sepsis, extensive surgery, acute illnesses, and the like. Patients in intensive care units are particularly prone to develop stress ulcers. Stress ulcers also include lesions that can lead to upper gastrointestinal bleeding; such bleeding is likely to be prevented by these compounds. NOSAC includes drugs such as ibuprofen, aspirin, indomethacin, naproxen, piroxicam and the like that are usually taken for analgesia, and that are often associated with gastrointestinal intolerance characterized by pain and lesions that may lead to bleeding. Lazaroids will be administered preferentially by the oral route either as tablets, capsules or liquids, in doses ranging from about 25 to about 500 mg, two to four times a day. The treatment would be either preventive, i.e., starting before ulcers have formed in patients at risk of developing such lesions, or therapeutic, i.e., once the ulcers have formed. In patients whose clinical condition precludes swallowing the oral dosage forms, lazaroids are given either through a nasogastric tube, or parenterally, i.e., IV or IM. The parenteral doses would range from about 5 to about 100 mg and be administered one to four times a day or by IV.

In dogs, lazaroids are useful in treating trauma, intervertebral diseases (slipped disk), traumatic shock, flea bite and other allergies.

In horses, lazaroids are useful in treating endotoxic or septic shock which follows colic, pretreatment before surgery for colic and treatment of Founder (laminitis). Lazaroids can reduce muscle damage that is a common occurrence during surgical procedures that require that the horse be prone for long periods during surgery.

In cattle, lazaroids are useful in treating acute coliform mastitis, bovine mastitis, acute allergic reaction to feed lot vaccination and shipping fever.

In pigs, lazaroids are useful in treating porcine stress syndrome and thermal stress syndrome.

The term treatment or treating as used in this patent is used broadly and includes both treatment of an existing condition as well as preventing the same condition from occurring where such is possible as is well known to those skilled in the art. For example, lazaroids can be used to treat existing asthma conditions and to prevent future ones from occurring. For example, lazaroids treat spinal trauma and prevent rejection of skin grafts.

Lazaroids can be used with each other and/or can be used with other pharmaceutical agents in treatment of the conditions listed above as is known to those skilled in the art.

In many instances it may be preferable to administer an inhibitor of lazaroids metabolism, such as ketoconazole or TAO (triacetyloleandomycin) prior to or concurrently with lazaroid administration to raise the blood level of the lazaroids and/or certain of its metabolites. Because females metabolize lazaroids more rapidly than males, administration of an inhibitor of lazaroids metabolism can raise blood levels in females to that of males. For example, ketoconazole should be administered in an amount of about 50 to about 300 mg/day, preferably about 200 mg/day about 1 to about 2 hr for acute uses and about 1 to about 3 hr for repeat dose situations.

Since agents such as phenobarbital and phenytoin decrease the blood levels of lazaroids, it is preferable to increase the dose of lazaroids given to individuals who either were taking or will be administered any agent which will decrease the blood level of lazaroids.

The sterile aqueous parenteral formulation of the present invention contains one or more lazaroids or a pharmaceutically acceptable salt, citrate (buffer), a cosolvent and water. Operable pharmaceutically acceptable acid addition salts include the hydrochloride, hydrobromide, hydroiodide, sulfate, phosphate, acetate, lactate, citrate, succinate, benzoate, salicylate, pamoate, cyclohexanesulfanate, methanesulfonate, naphthalenesulfonate, p-toluenesulfonate, maleate, fumarate and oxalate, preferred is the mesylate (monomethanesulfonate) salt. The amount of the lazaroid necessary is from about 0.9 to about 90 mg/ml of the free base or "free base equivalents". If the salt form is used a molar equivalent amount is necessary as is known to those skilled in the art.

The citrate is present for its buffering function. The buffer can be added as a buffering system (citric acid plus a salt of citric acid) or it can be generated in situ by adding either the acid or the salt of the acid and then adjusting the pH. Suitable citrate salts include sodium, potassium and ammonium and the equivalents there of. It is preferred to add the buffering system premade rather than generate it in situ. The operable amount of citrate is from about 0.002 to about 2.0M.

Operable cosolvents include for example the alcohols propylene glycol, polyethylene glycol, glycerol and ethanol as well as DMSO, DMAC, DMI and M-PYROL or their equivalents; it is preferred that the cosolvent be an alcohol selected from the group consisting of propylene glycol, polyethylene glycol, glycerol and ethanol, more preferably that the cosolvent be propylene glycol. The amount of the cosolvent necessary is any amount up to about 80%, depending on which particular cosolvent is used. It is preferred that the cosolvent be present in an amount of from about 1 to about 80%, more preferably from about 20 to about 60%. When the amount of the lazaroid to be solubilized is 25 mg/ml, it is preferred that the propylene glycol be present in about 40%.

Water is added in sufficient amounts to bring the mixture to volume.

The sterile aqueous parenteral formulation of the present invention is prepared as is known to those skilled in the art. More specifically and preferably the citrate buffers are dissolved in about 50 to about 70% of the available water. Next the cosolvent is added and mixed. Following addition of the cosolvent the drug is added, the pH adjusted and sufficient water added to volume. Optionally, the isotonicity can be adjusted to physiological levels, if that is desired the isotonicity adjusting agent is added when the citrate is added. Finally, the mixture is sterilized as is known to those skilled in the art.

The sterile aqueous pharmaceutical composition for parenteral administration is in concentrated form and is meant to be diluted (to the desired concentration of the lazaroid prior to administration to the patient. It can be diluted with physiological (normal or 0.9%) saline or 5% dextrose in water or mixtures thereof, or any other vehicle used in parenteral administration except for lactated Ringers solution. The critical requirement is the pH, if it is too high or buffered too high (over about 5) the lazaroid will precipitate out.

Alternatively, the sterile aqueous pharmaceutical composition for parenteral administration can be administered in its concentrated form. This is most likely to be performed in emergency situations where there is insufficient time for dilution. The only problem with administering the concentrated formulation is vascular irritation and damage. However, some emergency situation might justify this use. If done, it is recommended not to use this vein for follow up administration.

The sterile aqueous pharmaceutical composition for parenteral administration of the invention should be refrigerated, but not stored below −5°.

The sterile aqueous pharmaceutical composition containing a lazaroid for parenteral administration is useful for treating the conditions and/or diseases as set forth in U.S. Pat. No. 5,175,281 which can be treated by a parenteral dosage form, in the manner set forth in U.S. Pat. No. 5,175,281. As a parenteral pharmaceutical composition containing a lazaroid, it is useful in the same way as the pharmaceutical composition of U.S. Pat. No. 4,968,675.

The exact quantity and frequency of administration depends on the particular condition being treated, the severity of the condition being treated, the age, weight, general physical condition of the particular patient, other medication the individual may be taking as is well known to those skilled in the art and can be more accurately determined by measuring the blood level or concentration of a lazaroid in the patient's blood and/or the patient's response to the particular condition being treated.

DEFINITIONS AND CONVENTIONS

The definitions and explanations below are for the terms as used throughout this entire document including both the specification and the claims.

DEFINITIONS

All temperatures are in degrees Centigrade.

Tirilazad refers to 21-[4-[2,6-bis(1-pyrrolidinyl)-4-pyrimidinyl]-1-piperazinyl]-16α-methylpregna-1,4,9(11)-triene-3,20-dione.

5α-tirilazad refers to 21-[4-[2,6-bis(1-pyrrolidinyl)-4-pyrimidinyl]-1-piperazinyl]-16α-methyl-5α-pregna-1,9(11)-diene-3,20-dione.

5β-tirilazad refers to 21-[4-[2,6-bis(1-pyrrolidinyl)-4-pyrimidinyl]-1-piperazinyl]-16α-methyl-5β-pregna-1,9(11)-diene-3,20-dione.

6α-hydroxytirilazad refers to 6α-hydroxy-21-[4-[2,6-bis(1-pyrrolidinyl)-4-pyrimidinyl]-1-piperazinyl]-16α-methylpregna-1,4,9(11)-triene-3,20-dione.

6β-hydroxytirilazad refers to 6β-hydroxy-21-[4-[2,6-bis(1-pyrrolidinyl)-4-pyrimidinyl]-1-piperazinyl]-16α-methylpregna-1,4,9(11)-triene-3,20-dione.

"lazaroid" refers to the group of bispyrrolidinylpyrimidiylpiperazinylsteroids which includes tirilazad, 5α-tirilazad, 5β-tirilazad, 6α-hydroxytirilazad and 6β-hydroxytirilazad and pharmaceutically acceptable salts thereof.

Tirilazad mesylate refers to 21-[4-[2,6-bis(1-pyrrolidinyl)-4-pyrimidinyl]-1-piperazinyl]-16α-methylpregna-1,4,9(11)-triene-3,20-dione monomethanesulfonate salt.

TAO refers to triacetyloleandomycin.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When the solubility of a solid in a solvent is used the ratio of the solid to the solvent is weight/volume (wt/v).

qs ad refers to addition of a sufficient quantity of that material to bring the final composition to the specified volume.

DMSO refers to dimethylsulfoxide [$CH_3$—SO—$CH_3$].

DMAC refers to dimethylacetamide [$CH_3$—CO—N($CH_3$)$_2$].

DMI refers to dimethyl isosorbide.

M-PYROL refers to N-methyl-2-pyrrolidone.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

Preferred Formulation

| | |
|---|---|
| 21-[4-[2,6-bis(1-pyrrolidinyl)-4-pyrimidinyl]-1-piperazinyl]-16α-methylpregna-1,4,9(11)-triene-3,20-dione mesylate | 2.5 kg |
| citric acid, anhydrous | 4.42 kg |
| sodium citrate, hydrous | 588.0 g |
| propylene glycol | 40.0 l |
| pH adjust with acid/base to 2.9 | |
| water for injection, qs ad | 100.0 l |

The citric acid and sodium citrate are dissolved in about 25 l of water for injection. The propylene glycol is added to the citrate mixture and mixed thoroughly. The pH is adjusted to about 2.9. 21-[4-[2,6-bis(1-pyrrolidinyl)-4-pyrimidinyl]-1-piperazinyl]-16α-methylpregna-1,4,9(11)-triene-3,20-dione mesylate is added and dissolved. The pH is checked and adjusted if needed. Lastly qs ad with water for injection. The final mixture is then sterilized.

EXAMPLE 2

High Dose 21-[4-[2,6-Bis(1-pyrrolidinyl)-4-pyrimidinyl]-1-piperazinyl]-16α-methylpregna-1,4,9(11)-triene-3,20-dione mesylate And Low Buffer Ratio

| | |
|---|---|
| 21-[4-[2,6-bis(1-pyrrolidinyl)-4-pyrimidinyl]-1-piperazinyl]-16α-methylpregna-1,4,9(11)-triene-3,20-dione mesylate | 10.0 kg |
| citric acid, anhydrous | 10.8 kg |
| sodium citrate, hydrous | 1.18 kg |
| propylene glycol | 60.0 l |
| pH adjust with acid/base to 2.9 | |
| water for injection, qs ad | 100.0 l |

Following the general procedure of EXAMPLE 1 and making non-critical variations but using the ingredients above, the parenteral pharmaceutical composition is prepared.

EXAMPLE 3

High Buffer Ratio, Alternate Cosolvent

| | |
|---|---|
| 21-[4-[2,6-bis(1-pyrrolidinyl)-4-pyrimidinyl]-1-piperazinyl]-16α-methylpregna-1,4,9(11)-triene-3,20-dione mesylate | 1.0 kg |
| citric acid, anhydrous | 3.46 kg |
| sodium citrate, hydrous | 588.0 g |
| sodium chloride | 300.0 g |
| ethanol | 10.0 l |
| pH adjust with acid/base to 2.9 | |
| water for injection, qs ad | 100.0 l |

Following the general procedure of EXAMPLE 1 and making non-critical variations but using the ingredients above, the parenteral pharmaceutical composition is prepared.

EXAMPLE 4

Low Dose 21-[4-[2,6-Bis(1-pyrrolidinyl)-4-pyrimidinyl]-1-piperazinyl]-16α-methylpregna-1,4,9(11)-triene-3,20-dione mesylate, Low Propylene Glycol Concentration, In situ Buffer And Nearly Physiological Isosmotic

| | |
|---|---|
| 21-[4-[2,6-bis(1-pyrrolidinyl)-4-pyrimidinyl]-1-piperazinyl]-16α-methylpregna-1,4,9(11)-triene-3,20-dione mesylate | 100.0 g |
| citric acid, anhydrous | 115.3 g |
| sodium chloride | 850.0 g |
| propylene glycol | 1.0 l |
| pH adjust with acid/base to 2.9 | |
| water for injection, qs ad | 100.0 l |

Following the general procedure of EXAMPLE 1 and making non-critical variations but using the ingredients above, the parenteral pharmaceutical composition is prepared.

We claim:

1. A sterile aqueous pharmaceutical composition for parenteral administration which comprises:
   (1) about 0.9 to about 90 mg/ml of a lazaroid or a pharmaceutically acceptable salt thereof,
   (2) about 0.002 to about 2.0M citrate,
   (3) up to about 80% of a cosolvent selected from the group consisting of propylene glycol, polyethylene glycol, glycerol, ethanol, DMSO, DMAC, DMI and M-PYROL,
   (4) water at a pH of about 2.4 to about 3.5.

2. A pharmaceutical composition according to claim 1 where the lazaroid is selected from the group consisting of tirilazad, 5α-tirilazad, 5β-tirilazad, 6α-hydroxytirilazad and 6β-hydroxytirilazad.

3. A pharmaceutical composition according to claim 2 where the lazaroid is tirilazad.

4. A pharmaceutical composition according to claim 1 where the pharmaceutically acceptable acid addition salt is selected from the group consisting of hydrochloride, hydrobromide, hydroiodide, sulfate, phosphate, acetate, lactate, citrate, succinate, benzoate, salicylate, pamoate, cyclohexanesulfamate, methanesulfonate, naphthalenesulfonate, p-toluenesulfonate, maleate, fumarate and oxalate.

5. A pharmaceutical composition according to claim 4 where the pharmaceutically acceptable acid addition salt is methanesulfonate.

6. A pharmaceutical composition according to claim 2 where the lazaroid is tirilazad mesylate.

7. A pharmaceutical composition according to claim 1 where the amount of the lazaroid is from about 20 to about 40 mg/ml.

8. A pharmaceutical composition according to claim 1 where the amount of citrate is from about 0.25 to about 0.4M.

9. A pharmaceutical composition according to claim 1 where the cosolvent is selected from the group consisting of propylene glycol, polyethylene glycol, glycerol and ethanol.

10. A pharmaceutical composition according to claim 9 where the cosolvent is propylene glycol.

11. A pharmaceutical composition according to claim 1 where the amount of the cosolvent is present from about 1 to about 80%.

12. A pharmaceutical composition according to claim 11 where the amount of the cosolvent is present from about 20 to about 60%.

13. A pharmaceutical composition according to claim 1 where the pH is from about 2.7 to about 3.1.

14. A pharmaceutical composition according to claim 1 which is approximately isotonic.

15. A pharmaceutical composition according to claim 14 which is isotonic.

16. A pharmaceutical composition according to claim 1 where the molar ratio of total citrate buffer to lazaroid is from about 4.3:1 to about 14.5:1.

17. A sterile aqueous pharmaceutical composition for parenteral administration which comprises:
   (1) 25 mg/ml of 21-[4-[2,6-bis(1-pyrrolidinyl)-4-pyrimidinyl]-1-piperazinyl]-16α-methylpregna-1,4,9(11)-triene-3,20-dione mesylate,
   (2) 0.25M citrate,
   (3) 40% propylene glycol,
   (4) water at a pH of about 2.7 to about 3.1.

* * * * *